United States Patent [19]

de Nanteuil et al.

[11] Patent Number: 5,585,360

[45] Date of Patent: *Dec. 17, 1996

[54] PEPTIDE COMPOUNDS DERIVED FROM BORONIC ACID

[75] Inventors: Guillaume de Nanteuil, Suresnes; Christine Lila, Viroflay; Philippe Gloanec, La Celle Saint Cloud; Michel Laubie, Vaucresson; Tony Verbeuren, Vernouillet; Serge Simonet, Conflans Sainte Honorine; Alain Rupin, Savonnieres, all of France

[73] Assignee: Adir et Compagnie, Courbevoie, France

[ * ] Notice: The term of this patent shall not extend beyond the expiration date of Pat. No. 5,444,049.

[21] Appl. No.: 458,504

[22] Filed: Jun. 2, 1995

[30] Foreign Application Priority Data

Jun. 22, 1994 [FR] France ................................. 94 07589

[51] Int. Cl.⁶ .............................. A61K 38/06; C07F 9/22
[52] U.S. Cl. .............................. 514/19; 514/18; 530/331; 562/17
[58] Field of Search ........................ 514/18, 19; 530/331; 562/17

[56] References Cited

U.S. PATENT DOCUMENTS

| | | | |
|---|---|---|---|
| 5,187,157 | 2/1993 | Kettner et al. | 514/19 |
| 5,288,707 | 2/1994 | Metternich | 514/19 |
| 5,444,049 | 8/1995 | de Nauteuil et al. | 514/19 |

FOREIGN PATENT DOCUMENTS 0471651  2/1992  European Pat. Off. .

Primary Examiner—Jerry D. Johnson
Attorney, Agent, or Firm—The Firm of Gordon W. Hueschen

[57] ABSTRACT

The invention relates to the compounds of formula (I):

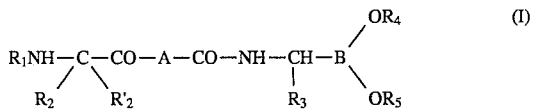

in which:

$R_1$ denotes hydrogen, acyl, alkoxycarbonyl, benzyloxycarbonyl, phenoxycarbonyl or linear or branched $C_1-C_6$alkyl, substituted or unsubstituted, or $R_6SO_2-$ in which $R_6$ denotes alkyl, naphthyl, phenyl, benzyl or morpholine, $R_2$ denotes hydrogen or phenyl, substituted or unsubstituted benzyl, thienylmethyl, (pyridyl)methyl, diphenylmethyl, fluorenyl, naphthylmethyl, benzocyclobutyl, (dicyclopropylmethyl)methyl, indanyl or $(C_3-C_7$ cycloalkyl)methyl, $R'_2$ denotes hydrogen or else $R_2$ and $R'_2$ together denote $C_6H_5-CH=$, $R_3$ denotes any one of the groups as defined in the description, each of $R_4$ and $R_5$ denotes hydrogen or alkyl, or

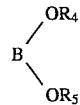

forms a boronic ester of pinanediol, A denotes the following group:

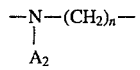

in which n and $A_2$ are as defined in the description, and medicinal products containing the same are useful as thrombin inhibitors.

9 Claims, No Drawings

PEPTIDE COMPOUNDS DERIVED FROM BORONIC ACID

BACKGROUND OF THE INVENTION

The present invention relates to peptide derivatives of boronic acid.

FIELD OF THE INVENTION

One of these serine proteases, thrombin, is the key enzyme in coagulation and plays a central part in the pathology of venous and arterial thromboses, as has been shown by F. Toti et at. (Sang, Thrombose, Vaisseaux, 4, 483–494, 1992) and T. M. Reilly et at. (Blood Coagulation and Fibrinolysis, 3,513–517, 1992).

The antithrombotic approaches are more effective and risk-free when compared with the present treatments. Direct inhibitors of thrombin, present under clinical development, exhibit a whole series of advantages over heparin. However, these substances, hirudin and hirulog-1 have the disadvantage of not being active when administered orally.

Furthermore, it is known that peptides containing the (D)Phe-Pro-Arg sequence are inhibitors of the catalytic site of thrombin (C. Kettner et at., J. Biol. Chem., 265 (30), 18289–18297, 1990).

DESCRIPTION OF THE PRIOR ART

Peptide derivatives of boronic acid exhibiting an antithrombotic activity have already been described in the literature. This is case more particularly with the compounds described in Patents EP 293,881 and EP 471,651. Furthermore, M. A. Hussain et al. have shown that Ac-(D)Phe-Pro-Arg-boronic acid (DUP 714) is an inhibitor of thrombin (Peptides, 12, 1153–1154, 1991).

It was therefore of particular interest to synthesize new inhibitors of serine proteases in order to increase the power, the selectivity and the activity, when administered orally, of the compounds already described in the literature.

DETAILED DESCRIPTION OF THE INVENTION

More specifically, the present invention relates to the compounds of formula (I):

$$R_1NH-\underset{\underset{R_2}{|}\ \underset{R'_2}{|}}{C}-CO-A-CO-NH-\underset{\underset{R_3}{|}}{CH}-B\underset{OR_5}{\overset{OR_4}{<}} \quad (I)$$

in which:

$R_1$ denotes a hydrogen atom, a linear or branched $C_1$–$C_6$ acyl, linear or branched $C_1$–$C_6$ alkoxycarbonyl, benzyloxycarbonyl, phenoxycarbonyl or linear or branched $C_1$–$C_6$ alkyl group (unsubstituted or substituted by one or more phenyl, carboxyl, linear or branched $C_1$–$C_6$ alkoxycarbonyl, phenoxycarbonyl, benzyloxycarbonyl or morpholinosulfonyl groups) or an $R_6SO_2$-group in which $R_6$ denotes a linear or branched $C_1$–$C_6$ alkyl, naphthyl, phenyl, benzyl or morpholine group (each of the naphthyl, phenyl or benzyl groups being itself optionally substituted by one or more halogen atoms or linear or branched $C_1$–$C_6$ alkyl, linear or branched $C_1$–$C_6$ alkoxy, trihalomethyl, amino, alkylamino or dialkylamino groups), $R_2$ denotes a hydrogen atom or one of the following groups:

phenyl, benzyl (unsubstituted or substituted on the phenyl nucleus by one or more halogen atoms or linear or branched $C_1$–$C_6$ alkyl, linear or branched $C_1$–$C_6$ alkoxy, hydroxyl, amino, nitro or carboxyl groups), thienylmethyl, pyridylmethyl, diphenylmethyl, fluorenyl, naphthylmethyl, benzocyclobutyl, (dicyclopropylmethyl)methyl, indanyl, or ($C_3$–$C_7$ cycloalkyl)methyl, $R'_2$ denotes a hydrogen atom or else $R_2$ and $R'_2$ together denote $C_6H_5$—CH=, $R_3$ denotes any one of the following groups:

$$\underset{RHN}{\overset{HN}{>}}C-S-(CH_2)_m-, \quad \underset{}{\overset{HN}{>}}CH-\underset{\underset{R^1}{|}}{N}-(CH_2)_m-,$$

$$\underset{R'HN}{\overset{HN}{>}}C-NH-(CH_2)_m-,$$

$$\underset{H_2N}{\overset{HN}{>}}CH-\underset{\underset{R'}{|}}{N}-(CH_2)_m- \quad \text{or,} \quad \underset{\underset{R}{N}}{\overset{N}{\diagdown}}\!\!-X-(CH_2)_m-$$

in which:

$1 \leq m \leq 6$,

R denotes a hydrogen atom or a linear or branched $C_1$–$C_6$ alkyl group,

R' denotes a linear or branched $C_1$–$C_6$ alkyl group,

X denotes a sulfur atom or an amino group, each of $R_4$ and $R_5$ denotes a hydrogen atom or a linear or branched $C_1$–$C_6$ alkyl group, or $$B\underset{OR_5}{\overset{OR_4}{<}}$$

forms a boronic ester of pinanediol,

A denotes the following group:

$$-\underset{\underset{A_2}{|}}{N}-(CH_2)_n-$$

in which:

n denotes 1 or 2, $A_2$ denotes a phenyl, indanyl, $C_3$–$C_7$ cycloalkyl (unsubstituted or substituted by one or more linear or branched $C_1$–$C_6$ alkyl groups), $C_3$–$C_7$ cycloalkenyl, bicyclo[2.1.1]hexyl or bicyclo[2.2.1]heptyl group or a group:

[structure: five-membered ring with X——Y]

in which

X and Y, which are different, denote an oxygen or sulfur atom or an NH or $CH_2$ group, their enantiomers, diastereoisomers and epimers and their addition salts with a pharmaceutically acceptable acid or base.

The invention also relates to the process for the preparation of the derivatives of formula (I), in which a protected amino acid of formula (II), whose isomers have optionally been separated by a conventional separation technique:

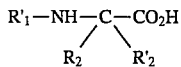 (II)

in which:

R'$_1$ denotes a linear or branched C$_1$–C$_6$ acyl, benzyl, linear or branched C$_1$–C$_6$ alkoxycarbonyl, benzyloxycarbonyl or phenoxycarbonyl group, R$_2$ and R'$_2$ have the same meaning as in formula (I), is reacted which is reacted according to the peptide coupling technique described by W. König and R. Geiger (Ber., 103, 788, 1970) with a second protected amino acid of formula (III) whose isomers have optionally been separated according to a conventional separation technique, $$HA-CO_2-CH_2C_6H_5 \quad (III)$$

in which A has the same meaning as in formula (I), in order to produce the compound of formula (IV):

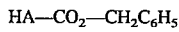 (IV)

in which R'$_1$, R$_2$, R'$_2$ and A have the same meaning as above, in which the acidic functional group is deprotected by catalytic hydrogenation or saponification, in order to produce the compound of formula (V):

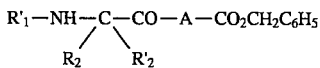 (V)

in which R'$_1$, R$_2$, R'$_2$ and A have the same meaning as above, which is reacted with N-hydroxysuccinimide in the presence of 1,3-dicyclohexylcarbodiimide in anhydrous medium, to produce the compound of formula (VI):

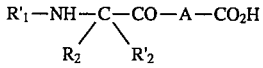 (VI)

in which R'$_1$, R$_2$, R'$_2$ and A have the same meaning as above and Suc denotes a succinimido radical, which is reacted in basic medium with a compound of formula (VII):

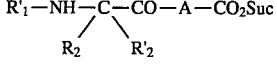 (VII)

in which:

R'$_3$ denotes the group Br—(CH$_2$)$_m$— in which m has the same meaning as in formula (I), each of R'$_4$ and R'$_5$ denotes a linear or branched C$_1$–C$_6$ alkyl group, or

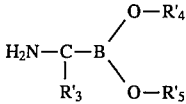

forms a boronic ester of pinanediol, to produce the compound of formula (VIII):

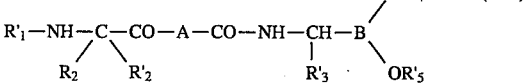 (VIII)

in which R'$_1$, R$_2$, R'$_2$, R'$_3$, A, R'$_4$ and R'$_5$ have the same meaning as above, which is reacted with optionally substituted thiourea or a compound suitable to obtain an appropriately substituted amine derivative, to produce the compound of formula (I/a), a particular case of the compounds of formula (I),

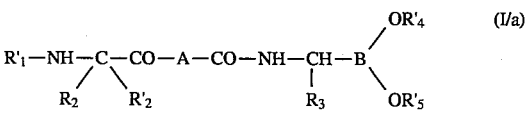 (I/a)

in which R'$_1$, R$_2$, R$_3$, R'$_2$, A, R'$_4$, R'$_5$, R and m have the same meaning as above, compound of formula (I/a) whose terminal amine functional group is deprotected if desired and which is converted, in inert medium, with the aid of boron trichloride, to the boronic acid of formula (I/b), a particular case of the compounds of formula (I):

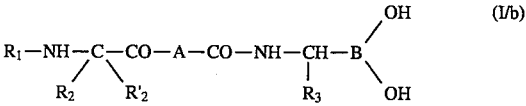 (I/b)

in which R$_1$, R$_2$, R'$_2$, A and R$_3$ have the same meaning as in formula (I), compound of formula (I/a) or (I/b):

which is optionally purified by a conventional purification technique, whose enantiomers are separated, if desired, by a conventional separation technique and which is converted, if appropriate, into its addition salts with a pharmaceutically acceptable acid or base.

Hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic, camphoric, oxalic and similar acids may be mentioned among the pharmaceutically acceptable acids, no limitation being implied.

Sodium hydroxide, potassium hydroxide, sodium bicarbonate and the like may be mentioned among the pharmaceutically acceptable bases, no limitation being implied.

The compounds of formula (VII) can be obtained from the compound of formula (IX) obtained according to the process described by M. W. Rathke et al. (J. Organomet. Chem., 122, 145–149, 1976):

 (IX)

in which R'$_4$ and R'$_5$ are as defined above, which is reacted with an organomagnesium compound of formula (X):

$$R'_3MgCl \quad (X)$$

in which R'$_3$ has the same meaning as above, to produce the compound of formula (XI):

 (XI)

in which R'$_3$, R'$_4$ and R'$_5$ are as defined above, which is reacted with 1,1,1,3,3,3-hexamethyldisilazane (HMDS) in the presence of n-butyllithium to produce the compound of formula (VII) after treatment in acidic medium.

The compound of formula (XI) can also be obtained by the process described by D. S. Matteson et al. (Organometallics, 3, 1284–1288, 1984) and W. Rathke et al. (J. Biol. Chem., 265(30), 18289–18297, 1990).

Apart from the fact that they are new, the compounds of the present invention exhibit particularly advantageous pharmacological properties.

They are powerful inhibitors of trypsin-like serine proteases which exhibit a high selectivity with regard to thrombin, when compared with other serine proteases of coagulation. Furthermore, they have a better activity when administered orally than the reference compound DUP 714.

These properties therefore make them useful in the treatment of stable or unstable anginas, of diseases of thrombotic origin and/or giving rise to thrombotic complications and in the treatment or the prevention of myocardial infarct and of venous or arterial thromboses.

They can also be employed in therapeutic combination with a thrombolytic agent.

The invention also extends to the pharmaceutical compositions containing at least one compound of formula (I) as active principle with one or a number of inert, nontoxic and appropriate excipients. The pharmaceutical compositions thus obtained can be presented in various forms, the most advantageous ones being tablets, coated tablets, gelatin capsules, suppositories, drinkable suspensions and the like.

The useful posology can be adapted depending on the nature and the severity of the disorder, the route of administration and according to the patient's age and weight. This posology varies from 1 to 500 mg daily in one or more doses.

The following examples illustrate the invention but do not limit it in any way.

The starting materials employed are starting materials which are known or prepared according to known procedures.

Preparation A produces a synthesis intermediate which is useful in the preparation of the compounds of the invention.

The structures of the compounds described in the examples and those of their intermediates have been confirmed by the usual spectroscopic techniques.

Preparation A: (+)-α-Pinanediol
(R)-1-amino-4-bromobutylboronate Hydrochloride

This compound was obtained by the process described by C. Kettner et al. (J. Biol. Chem., 265(30), 18289–18297, 1990) by reaction of allylbromide with catecholborane, followed by a transesterification with (+)-α-pinanediol, then a homologation reaction in the presence of dichloromethyllithium and finally the reaction with hexamethyldisilazane. Melting point: 160° C. Rotatory power: $[\alpha]_D^{25}=+16.5°$ (c=1%, ethanol)

| Elemental microanalysis: | | | | |
| --- | --- | --- | --- | --- |
| | C % | H % | N % | Cl % |
| Calculated | 45.88 | 7.15 | 3.82 | 9.67 |
| Found | 45.82 | 7.09 | 4.13 | 9.85 |

The abbreviations employed in the examples are the following:

Ac denotes acetyl,

Fmoc denotes 9-fluorenylmethoxycarbonyl,

Bz denotes benzyl,

Suc denotes the succinimido group, (R)Phe denotes the (R)-phenylalanyl residue,

Gly denotes the glycyl residue,

Boc denotes tobutoxycarbonyl.

Example 1: (+)-α-Pinanediol
1-(R)-{[Ac-(R)Phe-(N-cyclopentyl)Gly]amino}-4-(isothioureido)butylboronate Stage A: Boc-(R)Phe-(N-cyclopentyl)Gly-OBz By employing the peptide coupling (DCC/HOBT) technique described by W. König and R. Geiger (Ber., 103, 788, 1970) and anhydrous dimethylformamide as solvent, the expected product is prepared from 73 mmol of (N-cyclopentyl)Gly-OBz and from Boc-(R)Phe-OH and is purified by chromatography on a silica column, a dichloromethane/ethanol (97/3) mixture being employed as eluent. Yield: 76%

Stage B: H-(R)Phe-(N-cyclopentyl)Gly-OBz

The product obtained in the preceding stage is deprotected by dissolving 31 mmol in 150 ml of anhydrous ethyl acetate cooled in an ice-water bath while bubbling hydrochloric acid gas through for an hour. After return to ambient temperature and stirring for an hour, the mixture is evaporated. The residue is taken up in ether and reevaporated. Yield: 99%

Stage C: Ac-(R)Phe-(N-cyclopentyl)Gly-OBz 5 mmol of the compound obtained in the preceding stage in a mixture containing 10 ml of dioxane, 5 ml of water, 24 ml of acetic anhydride and 25 mmol of sodium bicarbonate are stirred at ambient temperature for 3 hours. After evaporation the residue is taken up with a water/ethyl acetate mixture. The organic phase is washed with water and then with a saturated sodium chloride solution. After drying and evaporation the expected product is obtained. Yield: 89%

Stage D: Ac-(R)Phe-(N-cyclopentyl)Gly-OH 5 mmol of the product obtained in the preceding stage in 25 ml of methanol are hydrogenated under a hydrogen pressure of 4 kg for 12 in the presence of 150 mg of anhydrous 10% palladium/C. After filtration of the catalyst the expected product is obtained after evaporation of the solvent.

Stage E: Ac-(R)Phe-(N-cyclopentyl)Gly-OSuc 4.46 mmol of the product obtained in the preceding stage in 20 ml of anhydrous dichloromethane are added to 4.46 mmol of N-hydroxysuccinimide in 50 ml of anhydrous dichloromethane, followed by 4.46 mmol of dicyclohexylcarbodiimide dissolved in dichloromethane. The whole is stirred for 12 hours at ambient temperature. After filtration of the dicyclohexylurea formed the expected product is obtained after evaporation.

Stage F: (+)-α-Pinanediol
1-(R)-{[Ac-(R)Phe-(N-cyclopentyl)Gly]amino}-4-bromobutylboronate 4 mmol of the compound obtained in preparation A in 10 ml of anhydrous dichloromethane and 4 mmol of the compound obtained in the preceding stage are placed under argon atmosphere at −20° C. 56 ml of triethylamine are then added dropwise and the whole is kept at −20° C. for 30 minutes. After return to ambient temperature the mixture is stirred overnight under argon atmosphere. After taking up with ethyl acetate, washing with water, with sodium bicarbonate, with water, with 0.2N hydrochloric acid and finally with water, the organic phase is dried and evaporated. The expected product is obtained after purification on "Sephadex®" resin. Yield: 90%

Stage G: (+)-α-Pinanediol
1-(R)-{[Ac-(R)Phe-(N-cyclopentyl)Gly]amino}-4-(isothioureido)butylboronate 2.4 mmol of the compound obtained in the preceding stage and 7.3 mmol of thiourea in 6 ml of ethanol are stirred at ambient temperature for 60 hours. After evaporation of the solvent the expected product is obtained after purification by being passed over "Sephadex®" resin, methanol being employed as eluent. Yield: 85%

Example 2: 1-(R)-{[Ac-(R)Phe-(N-cyclopentyl)Gly]amino}-4-(isothioureido)butylboronic Acid Acetate 2 mmol of the compound obtained in Example 1 in 25 ml of anhydrous dichloromethane are cooled to −78° C. under argon atmosphere. 8 mmol of boron trichloride are then added dropwise over 30 minutes. The temperature is brought to 0° C. and the whole is stirred for 30 minutes. 10 ml of iced water are then added and after stirring for 15 minutes, the mixture is brought to ambient temperature. The organic phase is separated off, extracted with 10 ml of a water/acetic acid (90/10) mixture. The remaining aqueous phase is washed with ether and the combined aqueous phases are evaporated. The residue is purified on Bio-gel, a water/acetic acid (90/10) mixture being employed as eluent, and produces the expected product, which is freeze-dried. The physicochemical analysis of the product is compatible with the expected structure. Mass spectrum: FAB$^+$:[M+glycerol-2H$_2$O+H$^+$]: m/z=561

Example 3: (+)-α-Pinanediol
1-(R)-{[Ac-(R,S)Phe-(N-cyclohexyl)Gly]amino}-4-(isothioureido)butylboronate The expected product is obtained by the process described in Example 1, by replacing, in stage A, (N-cyclopentyl)Gly-OBz with (N-cyclohexyl)Gly-OBz and Boc-(R)Phe-OH with Boc-(R,S)Phe-OH.

Example 4:
1-(R)-{[Ac-(R,S)Phe-(N-cyclohexyl)Gly]amino}-4-(isothioureido) butylboronic Acid Acetate The expected product is obtained by the process described in Example 2 from the compound described in Example 3.
Mass spectrum: FAB$^+$:[M+glycerol-2H$_2$O+H+]: m/z=576

Example 5: (+)-α-Pinanediol
1-(R)-{[Ac-(R)Phe-(N-cyclohexyl)Gly]amino}-4-(isothioureido )butylboronate The expected product is obtained by the process described in Example 1 by replacing, in stage A, (N-cyclopentyl)Gly-OBz with (N-cyclohexyl)Gly-OBz.

Example 6:
1-(R)-{[Ac-(R)Phe-(N-cyclohexyl)Gly]amino}-4-(isothioureido)butylboronic Acid Acetate The expected product is obtained by the process described in Example 2 from the compound described in Example 5.
Mass spectrum: FAB$^+$:[M+glycerol-2H$_2$O+H$^+$]: m/z=576

Example 7: (+)-α-Pinanediol
1-(R)-{[Ac-(R)Phe-(N-cyclopentyl)Gly]amino}-4-(1N-methylguanidino)butylboronate Stages A to F These stages are identical with Stages A to F of Example 1.

Stage G: (+)-α-Pinanediol
1-(R)-{[Ac-(R)Phe-(N-cyclopentyl)Gly]amino}-4-azidobutylboronate Stage H: (+)-α-Pinanediol
1-(R)-{[Ac-(R)Phe-(N-cyclopentyl)Gly]amino}-4-aminobutylboronate The products expected in stages G and H are obtained by the processes described in patent EP 615978.

Stage I: (+)-α-Pinanediol
1-(R)-{[Ac-(R)Phe-(N-cyclopentyl)Gly]amino}-4-(N-methylamino)butylboronate Benzenesulphonate 5.7 g of 3Å molecular sieve and 3.75 ml of a 40% strength aqueous solution of formaldehyde are added to 1 mmol of the compound obtained in the preceding stage in 20 ml of anhydrous ethanol. The whole is stirred at ambient temperature overnight. After filtration 1 mmol of benzenesulphonic acid is added to the ethanolic phases and the whole is hydrogenated in the presence of 100mg of 10% Pd/C as catalyst overnight at ambient temperature and atmospheric pressure. The expected product is obtained after filtration of the catalyst and purification on Sephadex® resin.

Stage J: (+)-α-Pinanediol
1-(R)-{[Ac-(R)Phe-(N-cyclopentyl)Gly]amino}-4-(1N-methylguanidino)butylboronate The expected product is obtained by reaction of the compound described in the preceding stage with cyanamide by the process described in Example 2 of patent EP 615978.

Example 8:
1-(R)-{[Ac-(R)Phe-(N-cyclopentyl)Gly]amino}-4-(1N-methylguanidino)butylboronic Acid Acetate The expected product is obtained by the process described in Example 2 from the compound described in Example 7.
Mass spectrum: FAB$^+$: [M+glycerol-2H$_2$O+H$^+$]: m/z=559

Example 9: (+)-α-Pinanediol
1-(R)-{[Ac-(R)Phe-(N-cyclohexyl)Gly]amino}-4-(1N-methylguanidino)butylboronate The expected product is obtained by the process described in Example 7 by employing (N-cyclohexyl)Gly-OBz as starting material.

Example 10: 1-(R)-{[Ac-(R)Phe-(N-cyclohexyl)Gly]amino}-4-(1N-methylguanidino)butylboronic Acid Acetate The expected product is obtained by the process described in Example 2 from the compound described in Example 9. Mass spectrum: FAB$^+$:[I$^+$]:[M+H$^+$]: m/z=516

Example 11: (+)-α-Pinanediol 1-(R)-{[Ac-(R)(3-amino)Phe-(N-cyclopentyl)Gly]amino}-4-(1N-methylguanidino)butylboronate

Stage A: (R,S)(3-Nitro)Phe-OH Hydrochloride

3-Nitrophenylalanine hydrochloride is obtained by reacting 3-nitrobenzyl bromide with ethyl acetamidomalonate in anhydrous ethanol medium and then by hydrolyzing the diethyl malonate formed with 6N hydrochloric acid in the presence of acetic acid.

Stage B: Fmoc-(R)(3-nitro)Phe-OH

To 4 mmol of the compound obtained in the preceding stage, dissolved in 14.4 ml of a 10% strength aqueous solution of sodium carbonate are added, after cooling, 4 mmol of Fmoc-Cl. After return to ambient temperature the whole is stirred overnight and then poured into 250 ml of water. The aqueous phase is washed with ether and acidified with concentrated hydrochloric acid to pH 1. The expected product, in racemic form, is filtered off, dried, and the isomers are separated by HPLC on preparative column DAICEL OD (eluant:heptane/isopropanol/trifluoroacetic acid:650/350/0.5).

Stage C: (R)(3-Nitro)Phe-OH

The product obtained in the preceding stage is deprotected in dioxane medium in the presence of piperidine.

Stage D: Boc-(R)(3-nitro)Phe-OH

The product obtained in the preceding stage is protected conventionally in the presence of di-t-butyl carbonate.

Stage E: Boc-(R)(3-nitro)Phe-(N-cyclopentyl)Gly-OBz

The expected product is obtained by the process described in stage A of Example 1 from the product obtained in the preceding stage.

Stages F to M

The products expected in these stages are obtained by the processes described in stages B to J of Example 7.

Example 12: 1-(R)-{[Ac-(R)(3-amino)Phe-(N-cyclopentyl)Gly]amino}-4-(1N-methylguanidino)butylboronic Acid Acetate The expected product is obtained by the process described in Example 2 from the compound described in Example 11. Mass spectrum: FAB$^+$:[I$^+$]:[M+M]$^+$: m/z=517

Example 13: (+)-α-Pinanediol 1-(R)-{[morpholinosulfonyl-(R)Phe-(N-cyclopentyl)Gly]amino}-4-(1N-methylguanidino)butylboronate The expected product is obtained by the process described in Example 7 by replacing, in stage A, Boc-(R)Phe-OH with the morpholinosulfonyl-(R)-Phe-OH described in J. Med. Chem. (Vol. 34, No. 7, p. 1937, 1991).

Example 14: 1-(R)-{[Morpholinosulfonyl-(R)Phe-(N-cyclopentyl)Gly]amino}-4-(1N-methylguanidino)butylboronic Acid Acetate The expected product is obtained by the process described in Example 2 from the compound described in Example 13.

Example 15: (+)-α-Pinanediol 1-(R)-{[Ac-(R)Phe-(N-cyclopentyl)Gly]amino}-4-(formimidoylamino)butylboronate

Stages A to H

These stages are identical with the stages A to H of Example 7.

Stage I: (+)-α-Pinanediol 1-(R)-{[Ac-(R)Phe-(N-cyclopentyl)Gly]amino}-4-(formimidoylamino)butylboronate The expected product is obtained by reacting, ethyl formimidate hydrochloride with the product obtained in the preceding stage by the process described in patent PCT/US94/04058.

Example 16: 1-(R)-{[Ac-(R)Phe-(N-cyclopentyl)Gly]amino}-4-(formimidoylamino) butylboronic Acid Acetate The expected product is obtained by the process described in Example 2 from the compound described in Example 15. Mass spectrum: FAB$^+$:[M+glycerol-2H$_2$O+H$^+$]: m/z=544

Example 17: (+)-α-Pinanediol 1-(R)-{[Ac-(R)Phe-(N-cyclopentyl)Gly]amino}-4-(N-methyl-N-formimidoylamino)butylboronate

Stages A to I

These stages are identical with the stages A to I of Example 7.

Stage J: (+)-α-Pinanediol 1-(R)-{[Ac-(R)Phe-(N-cyclopentyl)Gly]amino}-4-(N-methyl-N-formimidoylamino)butylboronate The expected product is obtained by the process described in stage I of Example 15 from the compound described in the preceding stage.

Example 18: 1-(R)-{[Ac-(R)Phe-(N-cyclopentyl)Gly]amino}-4-(formimidoylamino)butylboronic Acid Acetate The expected compound is obtained by the process described in example 2 from the compound described in Example 17. Mass spectrum: FAB$^+$:[M+glycerol-2H$_2$O+H$^+$]: m/z 32 545

Example 19: (+)-α-Pinanediol 1-(R)-{[Ac-(R)Phe-(N-cyclopentyl)Gly]amino}-4-[(2-imidazolyl)amino]butylboronate The expected product is obtained by the process described in Example 1 by replacing, in stage G, thiourea with 1-trityl-2-aminoimidazole and consequently carrying out an acidic hydrolysis.

Example 20: 1-(R)-{[Ac-(R)Phe-(N-cyclopentyl)Gly]amino}-4-[(2-imidazolyl)amino]butylboronic Acid Acetate The expected product is obtained by the process described in Example 2 from the compound described in Example 19. Mass spectrum: FAB$^+$:[M+glycerol-2H$_2$O+H$^+$]: m/z=555

Example 21: (+)-α-Pinanediol 1-(R)-{[Ac-(R)Phe-(N-cyclopentyl)Gly]amino}-4-[(1-methyl-2-imidazolyl)thio]butylboronate Stages A to F These stages are identical with the stages A to F of Example 1.

Stage G: (+)-α-Pinanediol 1-(R)-{[Ac-(R)Phe-(N-cyclopentyl)Gly]amino}-4-[(1-methyl-2-imidazolyl)thio]butylboronate 2 mmol of the bromo derivative obtained in stage F are added to a solution, cooled to 0° C., containing 2 mmol of sodium hydride and 2 mmol of 1-methyl-2-mercaptoimidazole in 10 ml of dimethylformamide. After return to ambient temperature, addition of water and extraction with ethyl acetate the expected product is obtained after drying and evaporation.

Example 22: 1-(R)-{[Ac-(R)Phe-(N-cyclopentyl)Gly]amino}-4-[(1-methyl-2-imidazolyl)thio]butylboronic Acid Acetate The expected product is obtained by the process described in Example 2 from the compound described in Example 21.

Pharmacological Study of the Compounds of the Invention

Example 23: Anticoagulant Activity, Measurement of the Thrombin and Prothrombin Times in Man In the presence of a standard quantity of thrombin or of calcium thromboplastin a normal plasma coagulates in a defined and constant time, called thrombin time (TT) and prothrombin time (PT) respectively. Venous blood is collected at the elbow bend into a trisodium citrate (0.109M) solution. A plasma depleted in platelets is obtained by centrifuging the blood samples (3000 g, 15 minutes).

The thrombin time is obtained with the Thrombin Prest (Stago) reagent and the prothrombin time with the Neoplastine (Stago) reagent. They are determined automatically by employing an ST4 (Stago) coagulometer. The antagonist or the solvent (10 1) is added to the plasma (90 1) and then incubated for 2 minutes at 37° C. 100 1 of thrombin or 200 1 of calcium thromboplastin are added and the stopwatch is started. In these conditions the TT obtained in the control plasma is of the order of 20 seconds in man, and PT of the order of 12 seconds. The activity of an inhibitor is evaluated by its ability to lengthen these times when compared with the control. In these conditions the compounds of the invention permit a lengthening of the thrombin time and of the prothrombin time of 50-fold and more. The effect of the inhibitors is measured and the concentration which doubles the coagulation time (CTT$_2$ for the thrombin time and CPT$_2$ for the prothrombin time) is determined. The results are reproduced in the following table:

| Products | CTP$_2$ (µM) | CTT$_2$ (µM) |
| --- | --- | --- |
| Example 2 | 2.29 | 0.20 |
| Example 4 | 2.44 | 0.34 |
| Example 6 | 2.92 | 0.29 |
| Example 8 | 3.06 | 0.30 |
| Ref.: DUP 714 | 2.63 | 0.18 |

Example 24: Inhibition of Thrombin and of Serine Proteases of Coagulation and Fibrinolysis In order to evaluate in vitro the inhibiting activity of the boro-Arginic products on human thrombin (Sigma, specific activity 3220 NIHU/mg), purified human fibrinogen (6M, Enzyme Research Laboratories) was added to a given quantity of thrombin (0.7 nM) previously incubated with or without the inhibitor to be tested (20° C., 10 minutes).

In order to evaluate in vitro the selectivity of these products in respect of different serine proteases of fibrinolysis and coagulation, the same protocol is applied to purified human plasmin (2 nM, Stago), to purified human activated protein C (2 nM, Stago), to purified human activated factor X (2 nM, Calbiochem), to the tissue activator of plasminogen (2 nM, Calbiochem), to purified human urokinase (2 nM, Choay), to purified human plasma kallikrein (2 nM, Calbiochem), using as substrates different peptide para-nitroanilides: <Glu-Phe-Lys-pNA (0.50mM, S 2403, Kabi) for plasmin, N-Cbo-Arg-Gly-Arg-pNA (0.39 mM, S 2765, Kabi) for the factor Xa<Glu-Pro-Arg-pNA (0.52 mM, S 2366, Kabi) for activated protein C, H-D-Pro-Phe-Arg-pNA (0.45 mM, S 2302, Kabi) for kallikrein, H-(D)-Ile-Pro-Arg-pNA (0.48 mM, S 2288, Kabi) for the tissue activator of plasminogen and <Glu-Gly-Arg-pNA (0.56 mM, S 2444, Kabi) for urokinase.

Inhibitors, enzymes and substrates are diluted in the same buffer (0.01 mM phosphate buffer, pH 7.4, containing 0.12M of sodium chloride and 0.05% of bovine albumin serum) and then distributed into a microplate made of polystyrene in a volume of 50 1.

The fibrin formed by the thrombin or the para-nitroanilide released by the action of the serine protease are measured spectrophotometrically at 405 nm after 5 or 30 minutes' reaction at 20° C. respectively.

The table below gives the concentration of compound inhibiting 50% of the enzyme activity (CI50) in the presence of the reference product (DUP 714) and of the compound of Example 2 when compared with the control without product. The results show that the compound of Example 2 inhibits thrombin as powerfully as DUP 7 14 but inhibits the other serine proteases of coagulation and of fibrinolysis much less than DUP 714. The compounds of Examples 2, 6 and 8 are therefore much more selective inhibitors of thrombin than DUP 714.

|  | Thrombin | Plasmin | tPA | Urokinase | FXa | Kalli | PCa |
|---|---|---|---|---|---|---|---|
| Ref. DUP 714 | 0.55 | 24 | 5.3 | 22 | 81 | 6.8 | 15 |
| Ex. 2 | 0.59 | 1038 | 108 | 2503 | >100000 | 164 | 593 |
| Ex. 6 | 1.75 | 1261 | 92 | 1508 | 10850 | 181 | 467 |
| Ex. 8 | 0.74 | >33000 | 395 | >33000 | >330000 | 1076 | 458 |

Example 25: Measurement of the Anticoagulant Activity Ex Vivo. Administration of the Products by Intravenous (I.V.) Route in the Rat OFA rats, fasted or not, are anaesthetized with pentobarbital (60 mg/kg, i.p.). The carotid artery and the jugular vein are exposed and catheterized. The catheters are purged with citrated physiological saline (1/40). After installation of the catheters a sampling of 1.5 cm$^3$ of arterial blood is performed on 0.109 M citrate (1/9).

- 30 minutes later the product to be tested is administered i.v. in a volume of 1 ml.
- Arterial samplings (1.5 ml) are then performed at 1 minute 30, 5, 15, 30 and 60 minutes.
- At each sampling 1.5 ml of citrated physiological saline is reinjected into the animal via the carotid.
- The tubes of blood are centrifuged for 5 minutes at 3000 g (preparation of the plasma).
- 100 1 of plasma are incubated with 100 1 of activated cephalin. The time of appearance of the coagulation phenomenon is measured after addition of 100 1 of calcium.
- The compounds of the invention, tested in a dosage of 0.25 mg/kg durably increase the activated cephalin time (ACT). The results are reproduced in the following table and show the indices of increase in the coagulation time.

|  | Time (minutes) | | | | |
|---|---|---|---|---|---|
|  | 1.5 | 5 | 15 | 30 | 60 |
| Ex. 2 | 2.6 | 1.8 | 1.2 | 1.2 | 1.1 |

Example 26: Measurement of the Anticoagulant Activity Ex Vivo. Administration of the Products by Intravenous Route (I.V.) in the Dog Fasted dogs are anaesthetized with pentobarbital (30 mg/kg, i.v.). A femoral artery and a saphenous vein are exposed and catheterized. The dogs are left breathing freely. The blood sampling procedures are identical with those described above for the rat in Example 5. The compounds of the invention tested in a dosage of 0.5 mg/kg durably increase the activated cephalin time (ACT). The increase in the ACT observed with the compounds of the invention is still significant 60 minutes after their administration and is not accompanied by a thrombopenia (see table).

| Product (dose) | Time (minutes) | ACT increase index | Range in the number of platelets (% of the control) |
|---|---|---|---|
| Example 2 | 1.5 | 9.6 | −3 |
| (0.5 mg/kg) | 5 | 3.6 | −2 |
|  | 15 | 1.9 | 0 |
|  | 30 | 1.4 | 0 |
|  | 60 | 1.1 | 0 |

DUP 714 in a dose of 0.25 mg/kg caused an increase in the ACT comparable with that obtained with Example 2 in a dosage of 0.5 mg/kg. This effect of DUP 714 was accompanied by a thrombopenia of 20%.

Example 27: Measurement of the Anticoagulant Activity Ex Vivo. Administration of the Products by Oral Route in the Dog After a blood sample has been taken, the products are administered orally. At specified times after the treatment the blood is sampled intravenously. The plasma is prepared, the platelets are counted and the thrombin time test is carried out.

The table shows that the product of Example 2 in a dosage of 2.5 mg/kg caused increases in the TT without modification of the number of platelets. The activity is durable (4 hours).

|  | Time (hours) | | | |
|---|---|---|---|---|
|  | 0.5 | 1 | 2 | 4 |
| Example 2 | 1.1 | 1.6 | 1.5 | 1.1 |

Example 28: Pharmaceutical Composition

Preparation formula for 1000 tablets with a dose of 10 mg:

| Compound of Example 2 | 10 g |
|---|---|
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

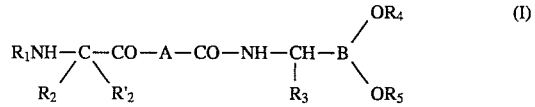

in which:

$R_1$ denotes hydrogen, linear or branched $C_1$–$C_6$ acyl, linear or branched $C_1$–$C_6$ alkoxycarbonyl, benzyloxycarbonyl, phenoxycarbonyl, or linear or branched $C_1$–$C_6$ alkyl which is unsubstituted or substituted by one or more phenyl, carboxyl, linear or branched $C_1$–$C_6$ alkoxycarbonyl, phenoxycarbonyl, benzyloxycarbonyl, or morpholinosulfonyl, or $R_6SO_2$— in which $R_6$ denotes linear or branched $C_1$–$C_6$ alkyl, naphthyl, phenyl, benzyl, or morpholine, each of the naphthyl, phenyl or benzyl being itself optionally substituted by one or more halogen or linear or branched $C_1$–$C_6$ alkyl, linear or branched $C_1$–$C_6$ alkoxy, trihalomethyl, amino, alkylamino, or dialkylamino, $R_2$ denotes hydrogen or one of the following groups:

phenyl,
benzyl (unsubstituted or substituted on the phenyl nucleus by one or more halogen or linear or branched $C_1$–$C_6$ alkyl, linear or branched $C_1$–$C_6$ alkoxy, hydroxyl, amino, nitro, or carboxyl),
thienylmethyl,
pyridylmethyl,
diphenylmethyl,
fluorenyl,
naphthylmethyl,
benzocyclobutyl,
(dicyclopropylmethyl)methyl,
indanyl, or
($C_3$–$C_7$ cycloalkyl)methyl, $R'_2$ denotes hydrogen or benzyl or else $R_2$ and $R'_2$ together denote $C_6H_5$—CH=, $R_3$ denotes any one of the following groups:

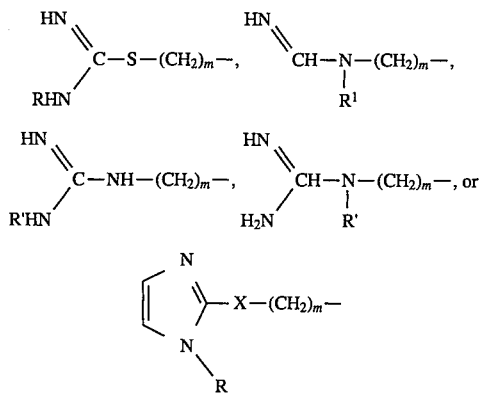

in which:
$1 \leq m \leq 6$,
R denotes hydrogen or linear or branched $C_1$–$C_6$ alkyl,
R' denotes linear or branched $C_1$–$C_6$ alkyl,
X denotes sulfur or amino, each of $R_4$ and $R_5$ denotes hydrogen or linear or branched $C_1$–$C_6$ alkyl, or

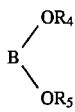

forms a boronic ester of pinanediol,

A denotes the following group:

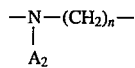

in which:
n denotes 1 or 2, $A_2$ denotes phenyl, indanyl, $C_3$–$C_7$ cycloalkyl (unsubstituted or substituted by one or more linear or branched $C_1$–$C_6$ alkyl), $C_3$–$C_7$ cycloalkenyl, bicyclo[2.1.1] hexyl, or bicyclo[2.2.1]heptyl, or:

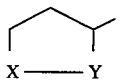

in which

X and Y, which are different, denote oxygen or sulfur or NH or $CH_2$, its enantiomers, diastereoisomers and epimers and its addition salts with a pharmaceutically-acceptable acid or base.

2. A compound of claim 1, wherein $R_1$ denotes an acetyl group, its enantiomers, diastereoisomers and epimers and its addition salts with a pharmaceutically-acceptable acid or base.

3. A compound of claim 1, wherein $R_2$ denotes a benzyl group, its enantiomers, diastereoisomers and epimers and its addition salts with a pharmaceutically-acceptable acid or base.

4. A compound of claim 1, wherein $R_3$ denotes a 3-(isothioureido)propyl group, its enantiomers, diastereoisomers and epimers and its addition salts with a pharmaceutically-acceptable acid or base.

5. A compound of claim 1, which is 1-(R)-{[Ac-(R)Phe-(N-cyclopentyl)Gly]amino}-4-(isothioureido)butylboronic acid, Ac denoting acetyl, (R)Phe denoting (R)-phenylalanyl, Gly denoting glycyl, its isomers and its addition salts with a pharmaceutically-acceptable acid or base.

6. A compound of claim 1, which is 1-(R)-{[Ac-(R)Phe-(N-cyclohexyl)Gly]amino}-4-(isothioureido)butylboronic acid, Ac denoting acetyl, (R)Phe denoting (R)-phenylalanyl, Gly denoting glycyl, its isomers and its addition salts with a pharmaceutically-acceptable acid or base.

7. A compound of claim 1, which is 1-(R)-{[Ac-(R)Phe-(N-cyclopentyl)Gly]amino}-4-(1N-methylguanidino)butylboronic acid, Ac denoting acetyl, (R)Phe denoting (R)-phenylalanyl, Gly denoting glycyl, its isomers and its addition salts with a pharmaceutically-acceptable acid or base.

8. A method for treating an animal or human living body afflicted with a condition requiring an inhibitor of thrombin comprising the step of administering to the living body an amount of a compound of claim 1 which is effective for alleviation of said condition.

9. A pharmaceutical composition useful as a thrombin inhibitor comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,585,360
DATED : December 17, 1996
INVENTOR(S) : G. de Nanteuil; C. Lila; P. Gloanec; M. Laubie; T. Verbeuren; S. Simonet; A. Rupin It is certified that error appears in the above-indentified patent and that said Letters Patent is hereby corrected as shown below:

Column 2, line 22 (approx.): In the right-hand formula, "$R^{1}$" should read -- $R'$ --.

Column 2, line 58: Insert -- ] -- at the end of the line after 2.1.1.

Column 2, line 59: Delete "]" from the beginning of the line.

Column 3, line 5: "(H)," should read -- (II), --.

Column 6, line 45: "palladiurn/C." should read -- palladium/C. --.

Column 7, line 21: "Example 2: 1-(R " should read -- Example 2: 1-(R)- --. Page 8, line 23.

UNITED STATES PATENT AND TRADEMARK OFFICE
CERTIFICATE OF CORRECTION

PATENT NO. : 5,585,360
DATED : December 17, 1996       Page 2 of 3
INVENTOR(S) : G. de Nanteuil; C. Lila; P. Gloanec; M. Laubie; T. Verbeuren; S. Simonet; A. Rupin It is certified that error appears in the above-indentified patent and that said Letters Patent is hereby corrected as shown below:

Column 7, line 22: Delete ")-" from the beginning of the line.

Column 9, line 10: "(N-c" at end of the line should read -- (N- --.

Column 9, line 11: "Insert -- c -- ahead of "yclopentyl)" at beginning of line.

Column 10, line 66: "32" should read -- = --.

Column 10, line 67: Delete "]:" at beginning of line, and Delete "32".

Column 11, line 1: Insert -- )- -- at end of line after "1-(R".

Column 11, line 2: Delete ")-" at beginning of the line.

Column 11, line 10: Insert -- )- -- at end of the line after "1-(R". Page 13, line 24

Column 11, line 18: Insert -- }- -- at end of line after "amino".

Column 11, line 19: Delete "}-" from beginning of the line.

UNITED STATES PATENT AND TRADEMARK OFFICE
CERTIFICATE OF CORRECTION

PATENT NO. : 5,585,360
DATED : December 17, 1996
INVENTOR(S) : G. de Nanteuil; C. Lila; P. Gloanec; M. Laubie; T. Verbeuren; S. Simonet; A. Rupin It is certified that error appears in the above-indentified patent and that said Letters Patent is hereby corrected as shown below:

Column 11, line 37: Insert ")-" at end of line after "(R".

Column 11, line 38: Delete ")-" from the beginning of the line.

Column 15, line 22: In the right hand formula, "$R^1$" should read -- $R'$ --.

Signed and Sealed this

Twenty-second Day of April, 1997

Attest:

BRUCE LEHMAN

*Commissioner of Patents and Trademarks*

*Attesting Officer*